(12) United States Patent
Newman et al.

(10) Patent No.: US 10,512,789 B2
(45) Date of Patent: *Dec. 24, 2019

(54) TOOTH-WHITENING DEVICE

(71) Applicant: THE PROCTER & GAMBLE COMPANY, Cincinnati, OH (US)

(72) Inventors: Matthew Lloyd Newman, Cincinnati, OH (US); Jayanth Rajaiah, Loveland, OH (US); Paul Albert Sagel, Maineville, OH (US); Elizabeth Lauren Keith, Ryland Heights, KY (US); Kimberly Horn Ellingson, Symmes Township, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/963,792

(22) Filed: Apr. 26, 2018

(65) Prior Publication Data

US 2018/0243581 A1  Aug. 30, 2018

Related U.S. Application Data

(63) Continuation of application No. 14/990,775, filed on Jan. 7, 2016, now Pat. No. 10,046,173.

(51) Int. Cl.
*A61N 5/06* (2006.01)
*A61C 19/06* (2006.01)

(52) U.S. Cl.
CPC .......... *A61N 5/0603* (2013.01); *A61C 19/066* (2013.01); *A61N 5/062* (2013.01); *A61N 2005/0606* (2013.01); *A61N 2005/0629* (2013.01); *A61N 2005/0652* (2013.01); *A61N 2005/0661* (2013.01); *A61N 2005/0663* (2013.01)

(58) Field of Classification Search
CPC ..... A61C 19/06; A61C 19/003; A61C 19/008; A61N 5/0603; A61N 5/0602; A61N 2005/0606; A61N 2005/0629; A61N 2005/0651

See application file for complete search history.

(56) References Cited

U.S. PATENT DOCUMENTS 5,309,277 A   5/1994  Deck
5,879,691 A   3/1999  Sagel et al.
(Continued)

FOREIGN PATENT DOCUMENTS

CN      201015606      2/2008
WO      WO03020160     3/2003
WO      WO2004011848   2/2004

*Primary Examiner* — Wade Miles
*Assistant Examiner* — Drew S Folgmann
(74) *Attorney, Agent, or Firm* — Vladimir Vitenberg

(57) ABSTRACT

A portable self-contained tooth-whitening device includes a compact housing structured and configured to be held in a fixed position adjacent to a human jaw during use; at least a first array of LEDs disposed in a first plane at a front side of the housing and arranged to deliver blue visible light or near-visible UV light of at least a threshold intensity to substantially all anterior surfaces of anterior maxillary teeth or anterior mandibular teeth of the human jaw, wherein the first array of LEDs forms at least two intersecting arcs, each of which is disposed in the first plane and has its own focal point located outside the device; and at least one battery cell powering the array of LEDs.

20 Claims, 8 Drawing Sheets

Fig. 3

(56) References Cited

U.S. PATENT DOCUMENTS

| | | |
|---|---|---|
| 5,891,453 A | 4/1999 | Sagel et al. |
| 6,949,240 B2 | 9/2005 | Sagel et al. |
| 8,241,035 B2 | 8/2012 | Jones et al. |
| 9,726,435 B2 | 8/2017 | Dahm |
| 9,752,748 B2 | 9/2017 | Jorgensen |
| 10,046,173 B2 | 8/2018 | Newman et al. |
| 2003/0152528 A1 | 8/2003 | Singh et al. |
| 2005/0026103 A1 | 2/2005 | Wasylicha |
| 2005/0158687 A1 | 7/2005 | Dahm |
| 2006/0019214 A1 | 1/2006 | Lawrence et al. |
| 2006/0134576 A1 | 6/2006 | West et al. |
| 2006/0167531 A1 | 7/2006 | Gertner |
| 2007/0054233 A1 | 3/2007 | Rizoiu et al. |
| 2008/0063999 A1 | 3/2008 | Osborn |
| 2008/0113313 A1 | 5/2008 | Khouri |
| 2010/0151407 A1 | 6/2010 | Rizoiu et al. |
| 2010/0220472 A1 | 9/2010 | Dahm |
| 2013/0027442 A1 | 1/2013 | Jorgensen |
| 2013/0045457 A1 | 2/2013 | Chetiar et al. |
| 2013/0295525 A1 | 11/2013 | Sagel et al. |
| 2015/0064645 A1 | 3/2015 | Jablow et al. |
| 2015/0140502 A1 | 5/2015 | Brawn et al. |
| 2016/0295202 A1 | 10/2016 | Evans et al. |
| 2016/0381749 A1 | 12/2016 | Catalano |

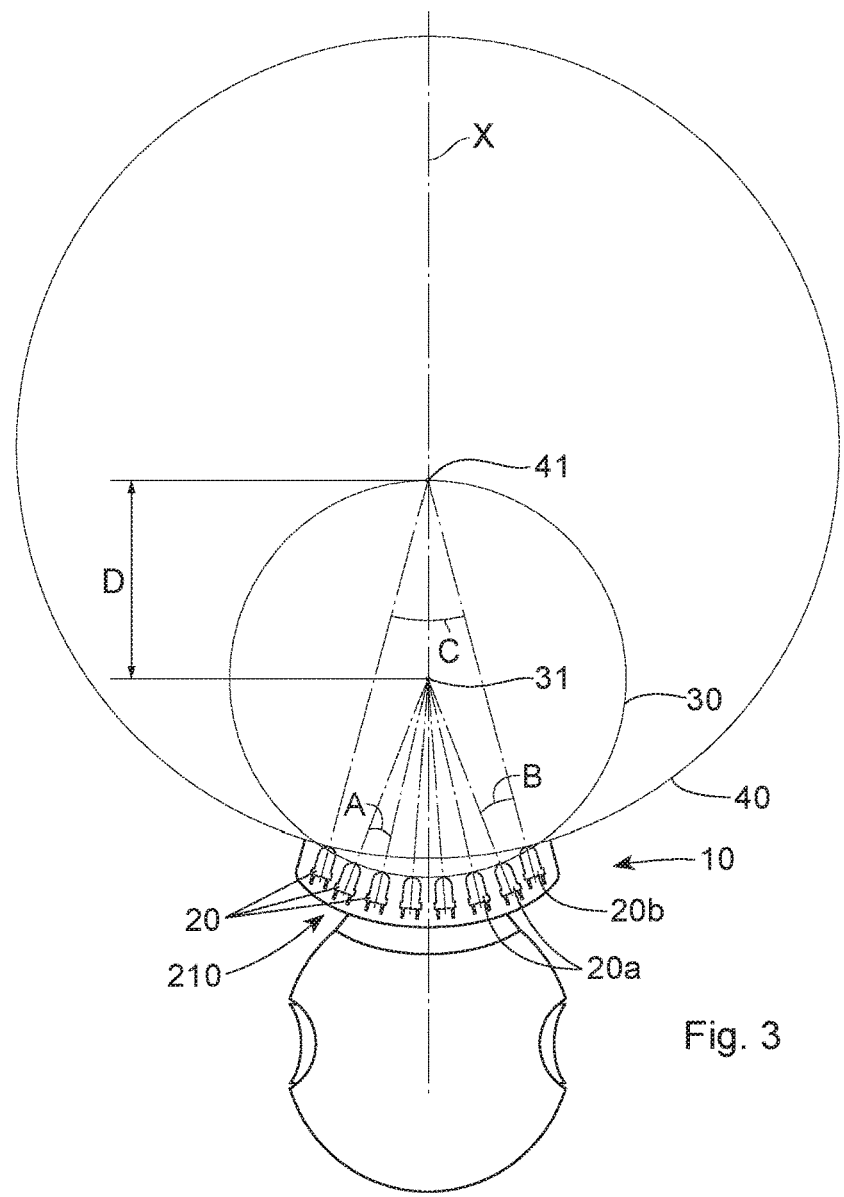
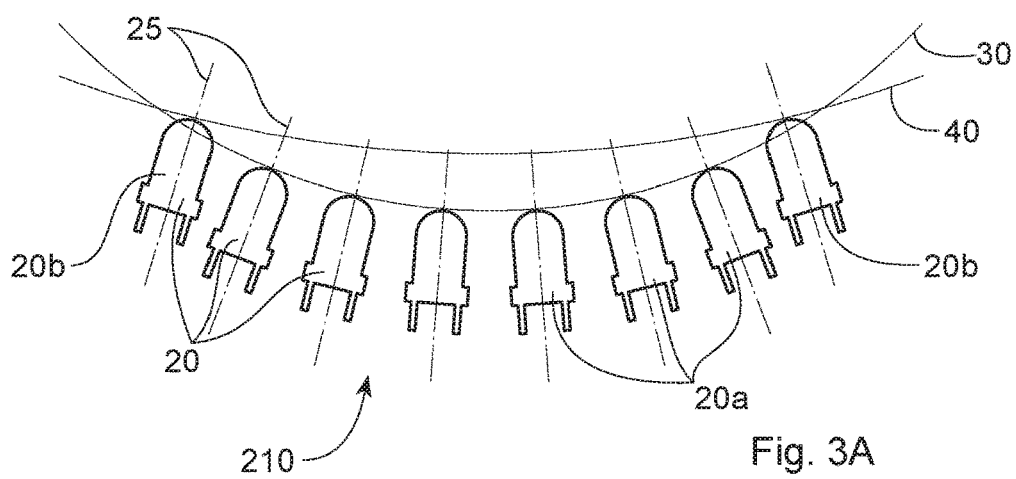
Fig. 3
Fig. 3A

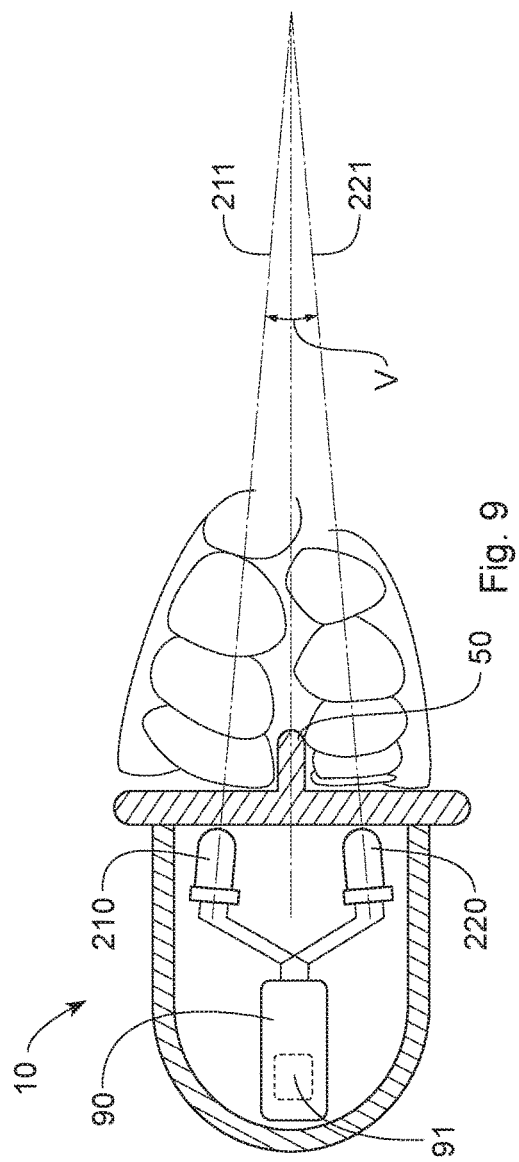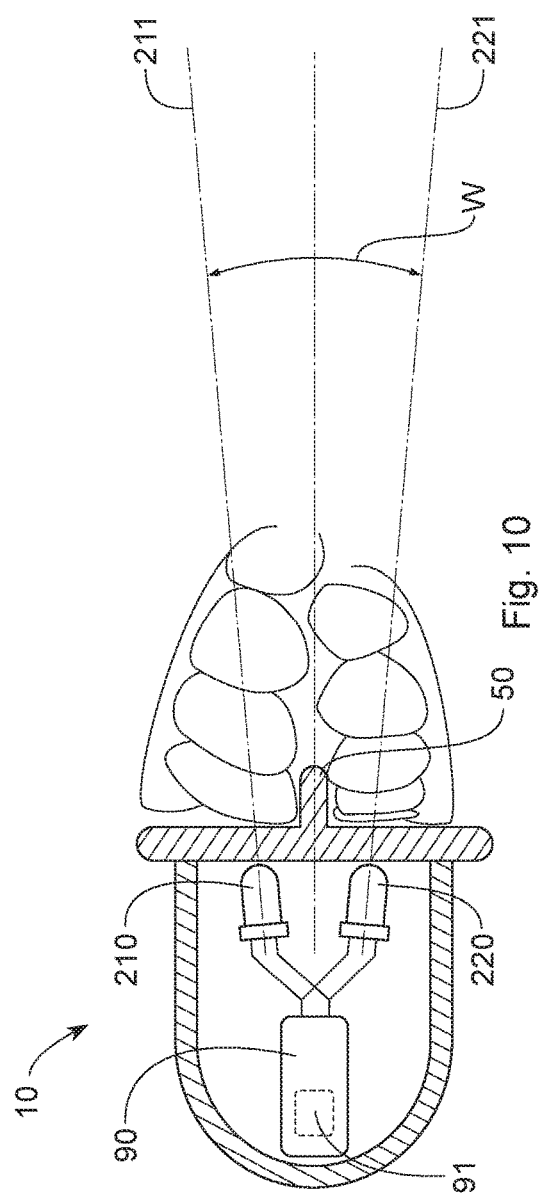

TOOTH-WHITENING DEVICE

FIELD OF THE INVENTION

This application relates to tooth-whitening devices and methods.

BACKGROUND

A number of approaches can be used to whiten teeth. One common approach is to use abrasives (e.g., in toothpastes and prophyaxis pastes) in combination with a polishing action to treat discolorations and stains on the surface of the teeth. Abrasives, however, offer limited effectiveness in whitening the teeth; because abrasives work only on the surface of the teeth, they do not appreciably change their intrinsic color.

Another approach is the use of chemical whitening actives in a composition to intrinsically and extrinsically whiten teeth. A chemical whitening active is applied to the teeth for a period of time to allow the active ingredient to act upon the teeth to provide an improvement in the whiteness of the teeth. Whiteners are commonly applied to the teeth via toothpastes, rinses, gums, floss, tablets, strips and trays.

A common chemical whitening active is Hydrogen peroxide ($H_2O_2$). Such common devices as plastic strips and trays can be used to apply peroxide for certain contact times beyond those achievable with typical tooth brushing. Concentration of the whitening active, contact time, and number of applications are some of the primary parameters that dictate the rate and amount of whitening achieved with peroxide-based tooth-whitening compositions. Whitening products using a strip of material in combination with a chemical whitening active are described, e.g., in U.S. Pat. Nos. 5,891,453 and 5,879,691, the disclosures of which are incorporated herein by reference.

Efforts to increase the efficacy of whitening products have included increasing the concentration of peroxide for faster whitening per time of use. Maintaining the peroxide on the tooth surface for longer contact times and/or for an increased number or frequency of applications has also been employed for improved whitening. While increasing concentration, increasing wear time, and increasing number of applications can achieve higher degrees of tooth whitening from a tooth-whitening product, each of these parameters also may have a negative impact on the consumer's experience.

Increasing the concentration of the peroxide in the whitening composition, while holding all other parameters essentially constant, can result in increased tooth sensitivity and soft-tissue irritation. Sufficiently high concentrations of peroxide may require a physical barrier, such as a rubber dam, to prevent the peroxide from contacting and burning the soft tissue, thereby making the use of the high peroxide concentrations inconvenient and impractical for unsupervised and repeated use, such as, e.g., repetitive at-home applications. In fact, even conventional tooth whitening compositions used by dentists and having a peroxide concentration equivalent to approximately 13% hydrogen peroxide, often require utilization of a rubber dam to protect the patient's soft tissue during the bleaching process during the office treatment. Increasing the use time and/or frequency generally increases the amount of tooth sensitivity and gingival irritation—and thus makes the product less convenient to use.

The mechanism of bleaching by peroxide involves the reduction of yellowness by generating singlet oxygen through the breakdown of hydrogen peroxide to convert $C=C$ bonds to carbon single bonds (C-x). $C=C$ bonds disproportionately absorb blue light (450 nm-470 nm) and thus appear as yellow under full-spectrum light, whereas C-x bonds do not. The acceleration of this chemical reaction under the application of blue light is reported widely in the literature, with one hypothesis being that application of blue light elevates outer-shell electrons in $C=C$ pairs to a higher quantum level, or energy state, increasing their ability to bond with available peroxide derivatives. The intensity of light needed to elevate electrons to a higher energy state is not known; however, the hypothesis supports the premise of a threshold intensity above which the reaction is accelerated and below which the reaction is not accelerated. To this end, it seems desirable to apply light above threshold intensity to as many teeth as possible, but it is of little benefit to deliver light substantially beyond the threshold intensity.

Use of blue light to accelerate teeth bleaching in the dental office has been in practice for more than ten years. Such companies as Zoom! and Britesmile provide high-power, high-intensity light-delivery systems to dental professionals for use with expert-applied, high-concentration peroxide chemistries such as carbamide peroxide and hydrogen peroxide. These systems are designed to provide light of sufficient intensity and of sufficient duration to accelerate whitening on all anterior surfaces of maxillary and mandibular teeth. However they have certain limitations, including lack of portability and comfort, requisite operator's skill, inflexible power requirements; and the process is time-consuming. More specifically, such systems are typically large, free-standing or floor-mounted appliances; that are designed to be operated exclusively by trained dental professionals (and cannot be self-administered); the application is typically uncomfortable to the patient and lasts for more than ten minutes—and in some cases multiple doses exceeding individually or in part ten minutes. In addition, such systems require the use of paint-on, high-concentration peroxide chemistries, along with including retractors and gingival barriers. Lastly, they are designed to be powered directly from 110 VAC power—as opposed to batteries.

A variety of blue-light devices exist in the market to deliver some form of light, typically blue light, to anterior surfaces of some teeth while said teeth are in the presence of peroxide chemistries. These devices fall into two categories: Rechargeable-cell-driven devices and primary-cell-driven devices. Rechargeable-cell-driven devices include at least one rechargeable battery, typically a Ni-Cad or Lithium chemistry battery, which by its nature and chemistry is capable of delivering a high current output relative to its capacity. Such cells are chosen for this attribute and are typically used also in applications requiring high current output, such as power tools, portable appliances, cellular telephones, etc. These cells provide an advantage in light-emitting tooth bleaching devices by supplying current at a very high intensity to an array of multiple light sources, such as LEDs, typically over a long duration, exceeding for example one minute, two minutes, five minutes, or ten minutes. The disadvantage of these devices is that they cannot be used for a full regimen of treatments, for example seven treatments, fourteen treatments, twenty treatments, or twenty-eight treatments, without being recharged at some point between treatments or doses. Recharging is an inconvenience to the user, adds complexity to the device, and necessitates typically an additional device or accessory to connect the device to mains power from the wall. Further, chemistries typically used in rechargeable battery cells do not maintain their charge and capacity during dormant periods as well as do the chemistries used in primary cell batteries.

Primary-cell-driven devices emitting light, including blue light, are typically limited in one of the three ways: (1) intensity of light delivered, (2) area coverage of teeth, or (3) physical weight of the device. Devices delivering high intensity light to a large area of teeth (including all maxillary and mandibular anterior teeth) typically have one or more heavy, large primary cells. Devices having a low total weight of primary cells, however, can typically deliver only low-intensity light to all intended teeth, or can deliver high intensity light only to a subset of all intended teeth. Further, many primary cells cannot deliver a full regimen of treatments including even two of three requirements (intensity, area coverage, and low weight) without the replacement of battery cells between treatments.

Therefore, it would be advantageous to provide a device that (1) delivers light of sufficient intensity and duration to effect photo-activated bleaching of teeth when peroxide-based chemistries are applied to teeth, (2) to cover substantially all of the anterior surfaces of the maxillary and mandibular anterior teeth and (3) to provide a full regimen of uses without replacement of any battery cell, and wherein (4) the device has a weight that allows a user to self-administer the device without the use of hands for almost the entire duration of a treatment period, e.g., about 90% or more of the dose time or the treatment period.

SUMMARY OF THE DISCLOSURE

The present disclosure is primarily directed to a delivery of light having intensity sufficient to accelerate peroxide-based teeth bleaching over the full array of a human subject's teeth substantially visible during an open-mouthed smile, given the limited electrical power available from primary-cell (single-use or disposable) batteries in a light-weight portable or disposable device that can be easily self-administered by an individual user. The light may be delivered over multiple doses of time periods, each lasting from approximately thirty seconds to approximately ten minutes, or from approximately two minutes to approximately five minutes. The optimal dose count may be as high as twenty, necessitating up to two hundred minutes of power delivery over the life of a device and its included battery set.

In one aspect, the disclosure is directed to a device comprising a compact housing structured and configured to be held in a fixed position adjacent to a human jaw during use. The device contains at least a first array of light-emitting diodes (LEDs) that are disposed in a first plane and at a front side of the housing. The LEDs are arranged to deliver blue visible light or near-visible UV light of at least threshold intensity at the teeth of about 13 mW/cm$^2$ to substantially all anterior surfaces of anterior maxillary teeth or anterior mandibular teeth of the human jaw. The first array of LEDs forms at least two intersecting arcs, each of which is disposed in the first plane and has its own focal point located outside the device. The LEDs are powered by one or more battery cells. The battery cells can be either primary, which are not rechargeable, or secondary, which can be recharged. In one embodiment, the primary cell or cells can be replaceable.

The light emitted by the LEDs during operation of the device may have a frequency of from 350 nm to 470 nm and may deliver the light above of at least a threshold intensity of 13 mW/cm$^2$. In use, the device provides a sequence of multiple tooth-whitening treatments without need for replacing or recharging the battery cell or cells. The device is light, having the total weight of not greater than 50 gram in one embodiment and not greater than 100 gram in another embodiment.

In one embodiment, the at least first array of LEDs comprises a plurality of outer LEDs and a plurality of inner LEDS, wherein the plurality of outer LEDs of the first array forms an outer arc having a first outer focal point, and the plurality of inner LEDs of the first array forms a first inner arc having a first inner focal point different from the first outer focal point, and wherein a distance between the first outer focal point and the device is greater than a distance between the first inner focal point and the device. In a further embodiment, the distance between the first outer focal point and the device is at least twice the distance between the first inner focal point and the device.

The plurality of the LEDs of the first array can be arranged so that an incremental angles between adjacent LEDs are within a range that would ensure an advantageous position of the focal point. For example, an incremental angle between axes of primary foci of two mutually adjacent inner LEDs of the first array can be between about 7 degrees and about 12 degrees. In a further example, an incremental angle between an axis of a primary focus of at least one of the inner LEDs of the first array and an axis of a primary focus of at least one of the outer LEDs adjacent thereto can be between about 7 degrees and about 12 degrees. In one embodiment, axes of primary foci of two mutually opposite end LEDs in the first array can form therebetween an included angle of from about 15 degrees to about 44 degrees, wherein the two mutually opposite end LEDs are the outer LEDs of the first array. Any suitable number of the LEDs can be used in the first array. Thus, the plurality of inner LEDs in the first array can include from 4 to 6 LEDs; and/or the plurality of outer LEDs in the first array can include from 2 to 4 LEDs.

In one embodiment, the device comprises a positioning feature that causes the first array of LEDs to direct the light primarily to either maxillary teeth or mandibular teeth. The positioning feature may have any suitable construction. In one exemplary embodiment, the positioning feature comprises a protrusion structured and configured to fit between the maxillary teeth or mandibular teeth of the user, so that the user can gently bit the positioning feature to secure the device in a desired position during use.

In one embodiment, the device can be structured to be invertible 180 degree, from a first orientation to a second orientation, wherein in the first orientation the light is primarily directed to maxillary teeth while in the second orientation the light is primarily directed to mandibular teeth. In such a configuration, the positioning feature can be structured to comfortably fit the user's mouth in either orientation, thereby facilitating the 180-degree versatility of the device.

In one embodiment, the device further comprises a second array of LEDs adjacent to the first array of LEDs. The second array of LEDs is disposed at a front side of the housing and in a second plane different from the first plane. The first plane and the second plane can (but do not have to) be mutually parallel. A distance between the mutually parallel first and second planes can be from about 0.5 cm to about 2.0 cm. In embodiments in which the first and second planes are not parallel, an included angle between the first plane and the second plane can be from about 0.5 degree to about 5 degree. In such a non-parallel configuration, the first and second arrays of LEDs can be arranged such that the light radiation emitted by the first array of LEDs and the second array of LEDs, respectively, either diverge or converge.

The second array of LEDs is also arranged to deliver blue visible light or near-visible UV light of at least a threshold intensity to substantially all anterior surfaces of anterior maxillary teeth or anterior mandibular teeth of the human jaw. Similarly to the first array of LEDs, the second array of LEDs forms at least two intersecting arcs, each of which is disposed in the second plane and has its own focal point located outside the device. Then, the first array of LEDs can be configured to deliver the light primarily to the maxillary teeth, while the second array of LEDs can be configured to deliver the light primarily to the mandibular teeth (or vice versa). The first array of LEDs and the second array of LEDs can be structured to be powered simultaneously. Alternatively, the first array of LEDs and the second array of LEDs can be structured to be powered sequentially. In a further embodiment, the first array of LEDs and the second array of LEDs can be structured to be powered in repetition at an established frequency. The LEDs of the first array and/or the LEDs of the second array can be powered sequentially, alternately, or variably.

In a further embodiment comprising two arrays of LEDs, the second array of LEDs can be substantially parallel to the first array of LEDs. In other words, a curved line formed by the LEDs of the first array (i.e., the curved line comprising the first inner arc and the first outer arc) is substantially parallel to a line formed by the LEDs of the second array (i.e., the curved line comprising the second inner arc and the second outer arc), wherein the first array is disposed above (or beneath depending of the orientation) the second array. In such a configuration, the LEDs of the second array can be either unilaterally stacked relative to the LEDs of the first array or unilaterally staggered relative to the LEDs of the first array. Staggered LEDs may, in some embodiments, provide a better light coverage as the adjacent staggered LEDs could achieve a close-packed structure than could be possible in a comparable stacked arrangement. In the staggered embodiment, one of the first and second arrays can have an odd number of LEDs and the other of the first and second arrays can have an even number. This could provide for left-right symmetry among the LEDs, if desired. A mixed stacked-staggered pattern (not shown) is also contemplated by this disclosure.

In another aspect, the disclosure is directed to a process of whitening human teeth. The process comprises providing at least a first array of light-emitting diodes (LEDs) disposed in a first plane and comprising a plurality of inner LEDs and a plurality of outer LEDs, wherein the plurality of inner LEDs of the first array forms a first inner arc having a first inner focal point, and the plurality of outer LEDs of the first array forms a first outer arc having a first outer focal point different from the first inner focal point, and wherein the first inner focal point and the second outer focal point are disposed on a first central axis common to the plurality of inner LEDs of the first array and the plurality of outer LEDs of the first array; applying a whitening composition to at least the anterior surfaces of at least six mandibular or maxillary anterior teeth and maintaining the whitening composition on the at least six teeth for a first time period; after the first time period, directing a light radiation comprising blue visible light or near-visible UV light of at least a threshold intensity from the least a first array of LEDs for a second time period to the anterior surfaces of the at least six teeth, the first time period having a duration greater than 50% of a total duration of the first time period and the second time period; and removing the whitening composition from the at least six teeth.

An incremental angle between axes of primary foci of two mutually adjacent inner LEDs of the first array can be between about 7 degrees and about 12 degrees. An incremental angle between an axis of a primary focus of at least one of the inner LEDs of the first array and an axis of a primary focus of at least one of the outer LEDs of the first array adjacent thereto is between about 7 degrees and about 12 degrees. Axes of primary foci of two mutually opposite end LEDs in the first array may be provided to form therebetween an included angle of from about 15 degrees to about 44 degrees, wherein the two mutually opposite end LEDs are the outer LEDs of the first array. The plurality of inner LEDs of the first array may include from 4 to 6 LEDs, and/or the plurality of outer LEDs of the first array may include from 2 to 4 LEDs. The LEDs can be conventionally powered by at least one battery cell that is either a primary cell, which is not rechargeable or user-serviceable, or a secondary cell, which is rechargeable.

In one embodiment, the process comprises at least a first treatment and a second treatment—and includes a step of inverting the first array of LEDs by 180 degrees, from a first orientation to a second orientation, wherein in the first orientation the light is primarily directed to the maxillary teeth during the first treatment, and in the second orientation the light is primarily directed to the mandibular teeth during the second treatment.

In another embodiment, the process comprises a step of providing a second array of LEDs adjacent to the first array of LEDs, wherein the second array of LEDs is disposed in a second plane different from the first plane, the second array of LEDs comprising a plurality of inner LEDs and a plurality of outer LEDs, wherein the plurality of inner LEDs of the second array forms a second inner arc having a second inner focal point, and the plurality of outer LEDs of the second array forms a second outer arc having a second outer focal point different from the second inner focal point, and wherein the second inner focal point and the second outer focal point are disposed on a second central axis common to the plurality of inner LEDs of the second array and the plurality of outer LEDs of the second array. In such an embodiment of the process, comprising providing two arrays of LEDs, the process may further include causing the first array of LEDs to deliver the light primarily to the maxillary teeth and causing the second array of LEDs to deliver the light primarily to the mandibular teeth.

In one embodiment of the process, comprising providing the first array of LEDs disposed in the first plane and the second arrays of LEDs disposed in the second plane, the second plane can be substantially parallel to the first plane. In an alternative embodiment (not shown), the second plane can be not parallel to the first plane, in which instance an included angle formed therebetween can be from about 0.5 degrees to about 5 degrees.

The second array of LEDs can be beneficially provided to be substantially parallel to the first array of LEDs. In such an embodiment, the LEDs of the second array can be unilaterally stacked relative to the LEDs of the first array. In an alternative embodiment, comprising the parallel first and second arrays of LEDs, the LEDs of the second array can be unilaterally staggered relative to the LEDs of the first array.

The process may comprise at least two treatments applied in sequence. The light can be applied in sequence to the maxillary teeth and the mandibular teeth during a single treatment. Alternatively or additionally, the light can be applied simultaneously to the maxillary teeth and the mandibular teeth during the single treatment.

The process may further comprise a step of simultaneously powering the first array of LEDs and the second array of LEDs. Alternatively or additionally, the process may comprise a step of sequentially powering the first array of LEDs and the second array of LEDs. The process may also comprise a step of powering the first array of LEDs and the second array of LEDs in repetition at an established alternating frequency.

BRIEF DESCRIPTION OF THE DRAWINGS

FIG. 3 schematically shows one exemplary arrangement of the LED array of an embodiment of the device.

FIG. 3A schematically shows an elevated view of a fragment of the LED array shown in FIG. 3.

FIG. 9 schematically shows a cross-sectional side view of an embodiment of the device comprising a first array of LEDs disposed in a first plane and a second array of LEDs disposed in a second plane, wherein the first plane and the second plane are mutually converging with respect to the light emitted by the LEDs of the first array relative to the light emitted by the LEDs of the second array.

FIG. 10 schematically shows a cross-sectional side view of an embodiment of the device comprising a first array of LEDs disposed in a first plane and a second array of LEDs disposed in a second plane, wherein the first plane and the second plane are mutually diverging with respect to the light emitted by the LEDs of the first array relative to the light emitted by the LEDs of the second array.

DETAILED DESCRIPTION

Figure 1:
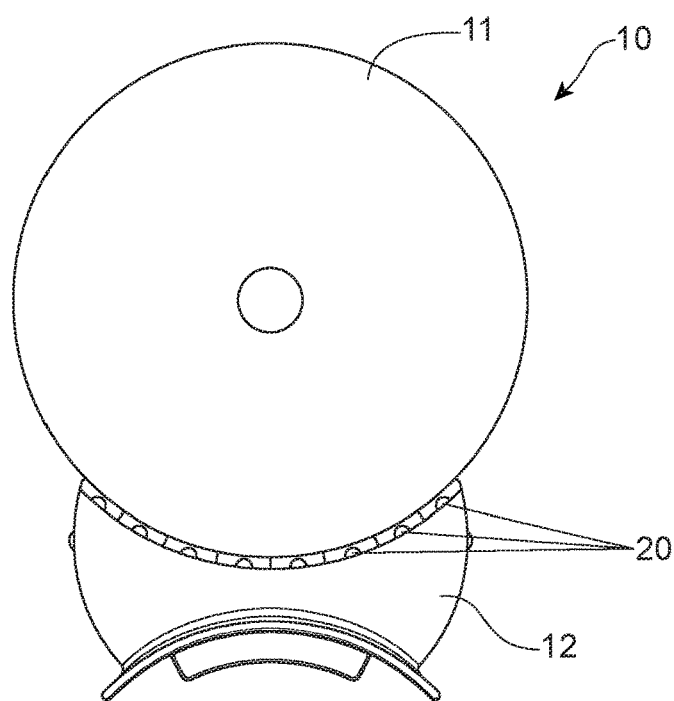
FIG. 1 schematically shows a top plan view of a device of the disclosure.
Figure 2:
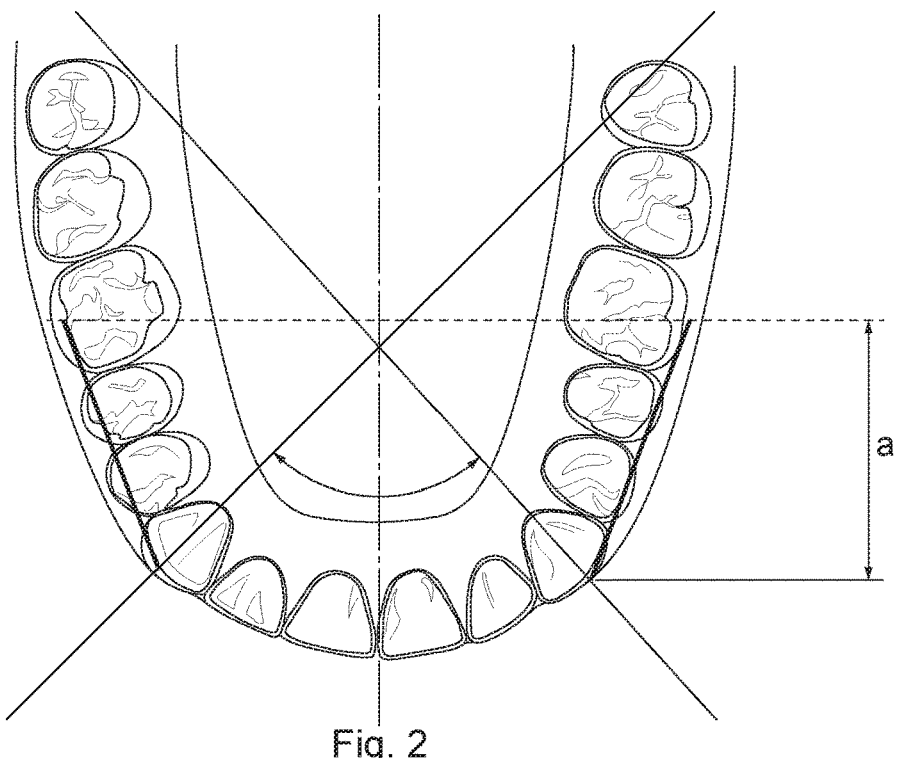
FIG. 2 schematically shows a generic plan approximation of a human jaw.

Blue light with a peak intensity of 450-470 nm has been demonstrated to accelerate tooth whitening when delivered at intensities exceeding 41.5 mW/cm$^2$, 108 mW/cm$^2$, or 134.7 mW/cm$^2$, see a commonly assigned US Patent Application Pub. No.: 2013/0295525 A1, the entire disclosure of which is incorporated herein by reference. Further clinical trials have shown that blue light with a peak intensity of 450-470 nm delivers accelerated tooth whitening over a tooth surface when delivered at peak intensities as low as 13 mW/cm2. If the typical human maxillary and mandibular anterior teeth surface area is approximately 10 cm$^2$, approximately 130-1300 mW of light with a peak intensity at 455-470 nm is expected to deliver whitening of all "smile" teeth.

Light-Emitting Diodes (LEDs) are familiar to those in the art as exemplary forms of delivery of substantially monotonic light ($\lambda^P_{1/2}$<50 nm) such as that used to demonstrate tooth whitening acceleration. Commonly reported efficiencies for blue LEDs mass-produced for commercial applications are around 0.35 W light output per 1.00 W power input (35% efficient). A perfectly designed array of LEDs thus requires 0.371-3.7 W total power to completely cover the indicated area completely and simultaneously.

For dose times of 120 s-300 s, indicated by the above-mentioned US 2013/0295525, this requires a minimum of 44.5-1110 J of electrical energy per dose. Delivery of electrical power to LEDs is understood by those familiar with the art to require special electronics, as LEDs are most safely and effectively driven by a stable electrical source, which batteries are not. Such electronics may themselves consume power comparable to that consumed by the LEDs. In this instance, 90-2000 J of electrical energy per dose is a more accurate estimate.

Further, it is known to those familiar with the art that the intensity of light delivered by LEDs decreases with the distance from the LED, including such LEDs as are encased in optical plastic to form focusing bulbs or lenses. Doubling the distance from LED to the treatment area from 1 mm to 2 mm may decrease intensity by half. Further doubling the distance from 2 mm to 4 mm may decrease intensity further by half. Because mandibular anatomy varies widely among individuals, one may rightly assume that, to deliver effective whitening, the light intensity prescribed should exceed, by as much as 100% or 200% or more, the minimum intensity proven to deliver benefits to perfectly smooth and equidistant surfaces.

A device designed to provide light incident to anterior teeth surfaces for 120 s-300 s must be held in place by some means. It is a common method for such devices to include features, such as buttresses or trays, which may fit between gums and lips, or between the mandibular and maxillary arches of teeth, to allow said device to be held in constant position without the use of hands. Hand, of course, may be used to install or remove the device, but the intent is for the device to be effectively hands-free in use. For a device to be hands-free and stay in position with minimal discomfort, it must not cause an excessive bending moment to a user's load-bearing oral surfaces where the device is mounted. This bending moment can be minimized by minimizing both a weight and a physical size of the device—and especially a distance between the device's center of mass and the user's mouth. To maximize comfort to the user, it is desirable to maintain the weight below about 100 g, specifically below about 50 g, and even more specifically below about 35 g. A reduction in the device's weight, however, appears to be in direct contradiction to the device's ability to provide sufficient electrical power by means of portable battery cells.

Table 1 shows the published capacity of several primary cell types. Given these data, and the considerations explained herein above, it seems clear that 15-20 gram of primary-cell batteries can possibly deliver an intensity of light to teeth that is substantially above the threshold for many varying individual subjects' anatomies. However it is not obvious how every array of LEDs may deliver such light.

TABLE 1

Published Capacity of Primary Cells, by Type

| Cell type (chemistry) | Maximum Capacity @ 1 mA current draw | Typical Capacity @ 100 mA current draw | Weight (g) | Energy/Weight Ratio (J/g) |
|---|---|---|---|---|
| CR2430 (LiMnO$_2$) | 270 mAh @ 3 V (2916J) | <250 mAh @ 1.5 V (J) | 4.6 | 634 |
| CR2450 (LiMnO$_2$) | 620 mAh @ 3 V (6696J) | <600 mAh @ 1.5 V (J) | 6.8 | 984 |
| AAA (Alkaline) | 900 mAh @ 1.5 V (4860J) | <900 mAh @ 1.2 V (J) | 11.0 | 441 |
| AA (Alkaline) | 2400 mAh @ 1.5 V (12960J) | 2400 mAh @ 1.2 V (J) | 24.0 | 540 |
| 9 V (Alkaline) | 400 mAh @ 9 V (12,960J) | 400 mAh @ 4.5 V | 45.6 | 284 |

While one can roughly model, to a first approximation, the human jaw by a circular arc, this approximation typically loses accuracy between the lateral incisor and molar teeth. An improved approximation is a circular arc connected with tangent lines, as is shown in FIG. 1, in which a circular arc outlining anterior surfaces of maxillary anterior teeth are approximated with a line MA and anterior or labial surfaces of posterior/molar teeth are approximated with a line PM. For such an approximate array of tooth surfaces, an LED-array design comprising a single arc is unlikely to deliver adequate light intensity to canine teeth CT without also delivering insufficient intensity to incisors IT.

One approach to solving this problem is to deliver excess current to outer LEDs, in comparison to inner LEDs, in a single circular-arc array. This solution, however, has the disadvantage of requiring additional complexity in electronics. An alternative solution is to provide a general form for an LED arrangement which would more uniformly deliver light intensity to each indicated tooth and provide for the delivery of light of gradually decreasing intensity from indicated anterior teeth to non-indicated posterior teeth in more uniform fashion. While the need to deliver light having gradually decreasing intensity may seem contradictory to the hypothesis of accelerated bleaching via elevation of electron-energy levels to discrete quantum states, it must be noted that time and imprecise placement of a device also play a role in photo-activated bleaching, and thus gradual intensity variation from indicated to non-indicated teeth is preferred.

In one embodiment, a portable, self-contained, lightweight device 10 includes a compact housing 11 and at least a first array of cylindrical or elliptical LEDs 20 disposed therein, FIGS. 1-8. The devise is "portable" because it is of a relatively small size and is designed to be conveniently manipulated by the user's hands and easily adjustable in use relative to the user's teeth/jaw. The device is "self-contained" (or self-sufficient) because it is autonomous and designed to operate independently of any external power source or any additional hardware equipment. The device 10 includes at least one battery cell 91, which can be part of a suitable electronic unit 90, FIGS. 6-8. The cell 91 can be a primary cell, which is not rechargeable or user-serviceable, or a secondary cell, which is rechargeable. A total weight of the device can advantageously be not greater than 100 g, and more specifically not greater than 50 g.

Figure 4:
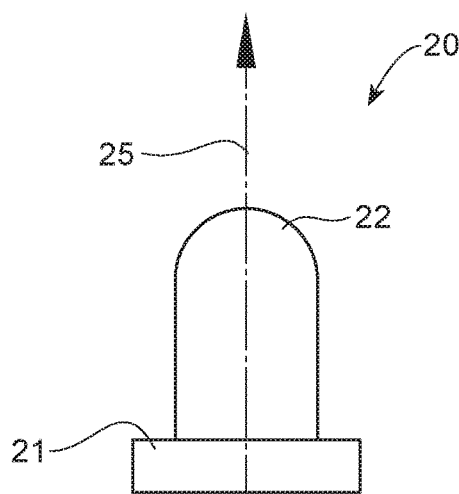
FIG. 4 schematically shows an elevated side view of an exemplary LED having an axis of primary focus defined as an axis along which the intensity of light is highest.
Figure 4A:
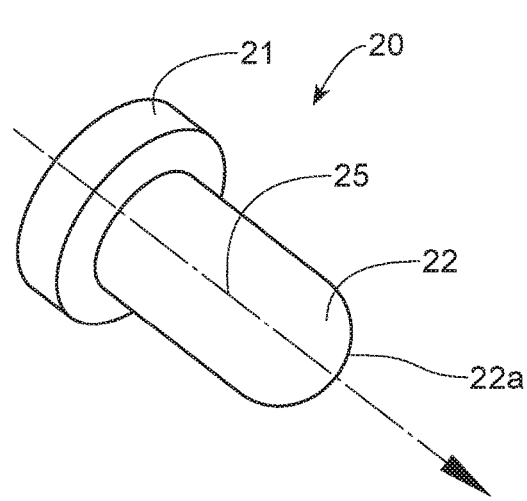
FIG. 4A schematically shows an axonometric view of the exemplary LED shown in FIG. 4.
Figure 5:
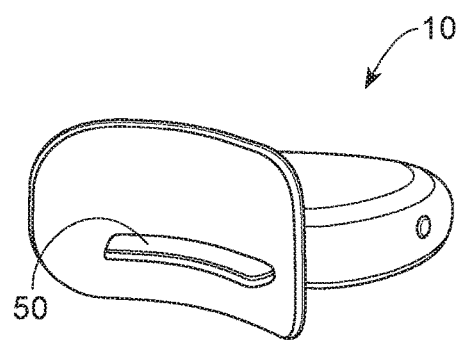
FIG. 5 schematically shows an axonometric view of an embodiment of the device of the disclosure.
Figure 5A:
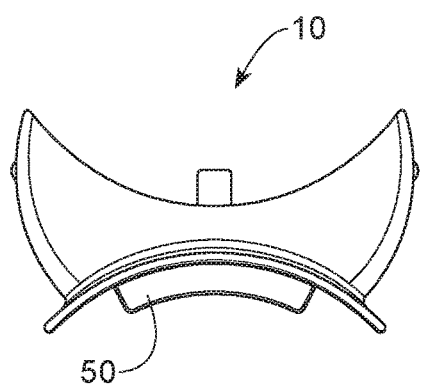
FIG. 5A schematically shows a plan view of the embodiment shown in FIG. 5.

The individual LED 20 in the at least a first array includes a power-connection end 21 and a light-emitting end 22, FIGS. 4 and 4A. The power-connection end 22 may comprise power-connection leads (not shown) through which an electrical current can be driven. The light-emitting end 22 may comprise spherical or ellipsoidal light-emitting tip 22a, FIG. 4A. The luminous intensity of light-emitting diodes is typically measured in millicandelas (mcd), or thousandths of a candela. The tip 22a of each LED 20 can emit at least 600 mcd of light when at least 5 mA of electrical current is applied through the power-connection leads at the power-connection end 21. Alternatively, the tip 22a of each LED 20 can emit at least 120 mcd of light under 1 mA of applied current.

Each LED 20 has an axis of primary focus 25, defined herein as an axis along which the LED-emitted light has the highest intensity, wherein the light intensity gradually decreases radially away from the axis of primary focus. In an embodiment of the LED 20 shown in FIGS. 4 and 4A, the axis of primary focus 25 of the LED coincides substantially with the axis of radial symmetry of cylindrical/spherical and/or cylindrical/ellipsoidal LED 20 and coincides substantially with the axis formed by two planes intersecting major and minor axes of the LED 20 with a substantially elliptical cross section.

The at least first array of LEDs 20 can be arranged such that all LED axes of primary focus 25 lie substantially in a single plane. Naturally, the focal point or points of the primary foci 25 of the array of LEDs will also lie in the same plane. One embodiment of the LED array is schematically shown in FIGS. 3 and 3A, wherein the LEDs 20 in the array are oriented with the tips 22a of their light-emitting ends 22 substantially arranged in two arcs: an inner arc 30 and an outer arc 40. The inner arc 30 is formed by a plurality of inner LEDs 20a, and the outer arc 40 is formed by a plurality of outer LEDs 20b. In the exemplary embodiment of FIGS. 3 and 3A, there are six inner LEDs 20a and two outer LEDs 20b.

The inner arc 30 and the outer arc 40 may lie substantially in a single plane, in which instance the primary foci 25 of the inner LEDs and the outer LEDs will also lied in a single pane, as is shown in several figures. Alternatively, the inner arc 30 and the outer arc 40 may lie in different planes, in which instance the primary foci 25 and the primary foci of the outer LEDs may form an included angle therebetween.

The inner arc 30 and the outer arc 40 have two focal points, because the primary axes of the foci 25 of the LEDs 20 form two distinct focal points: an inner-arc focal point 31, formed by the primary foci 25 of the inner LEDs 20a, and an outer-arc focal point 41, formed by the primary foci 25 of the outer LEDs 20b. Both focal points 31, 41 exist externally relative to the device 10, with the inner-arc focal point 31 being substantially closer to the device 10 than the outer-arc focal point 41. A distance D (FIG. 3) between the inner focal point 31 and the outer focal point 41 can be from about 20 cm to about 100 cm. In one embodiment, a distance between the outer focal point 41 and any LED's light-emitting tip 22a is at least twice as great as a distance between the inner focal point 31 and any LED's light-emitting tip 22a. The device 10 may have two arrays of LEDs, arranged either in parallel to one another or otherwise, as is explained herein below.

It is conceivable that the provision of light of sufficient intensity may not be adequate for all users, e.g., users with especially large or tall teeth, or teeth having unusually inclined surfaces and other atypical features or irregularities. In that instance, it may be desirable to indicate separate treatments for each maxillary and mandibular arch. To facilitate positioning of the device 10 to deliver the optimal light intensity, one may wish to provide a locating or positioning feature 50, such as, e.g., a protrusion, a boss or a ledge, which can be used as a geometrical point of reference and against which a user can locate the maxillary and/or mandibular anterior teeth. Non-limiting examples of the device 10 having such a positioning feature 50, comprising a protruding bar/ledge, are shown in FIGS. 5-8.

The positioning feature 50 can be incorporated into the device 10 to indicate to the user the desired placement of the device 10 relative to the user's teeth being treated. For example, an "upright" position, best adopted for whitening maxillary teeth, can be defined as a "first orientation" (FIGS. 6 and 7); and a "downward" position, best adapted for bleaching mandibular teeth, can be defined as a "second orientation" (FIG. 7A). In the embodiment of the device 10 shown in FIGS. 7 and 7A, the second orientation (FIG. 7A) is an inversion of the first orientation (FIG. 7) with respect to the plane containing the LED axes of primary foci. Thus, the embodiment of the device 10 shown in FIGS. 7 and 7A is invertible 180 degrees, from a first orientation to a second orientation, wherein in the first orientation, shown in FIG. 7, the light is primarily directed to the maxillary teeth, while in the second orientation, shown in FIG. 7A, the light is primarily directed to the mandibular teeth.

Figure 6:
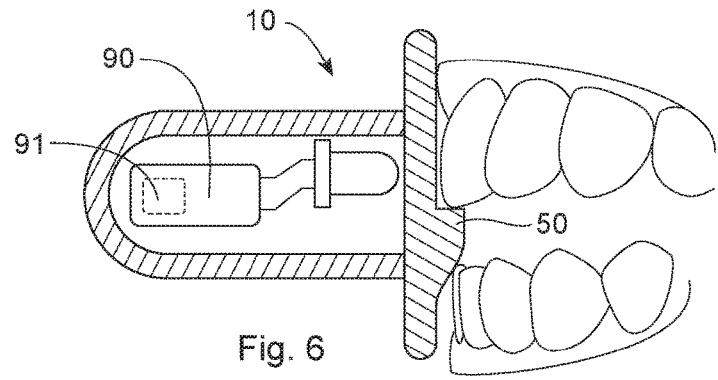
FIG. 6 schematically shows a cross-sectional side view of an embodiment of the device wherein the light is primarily directed to maxillary teeth.
Figure 7:
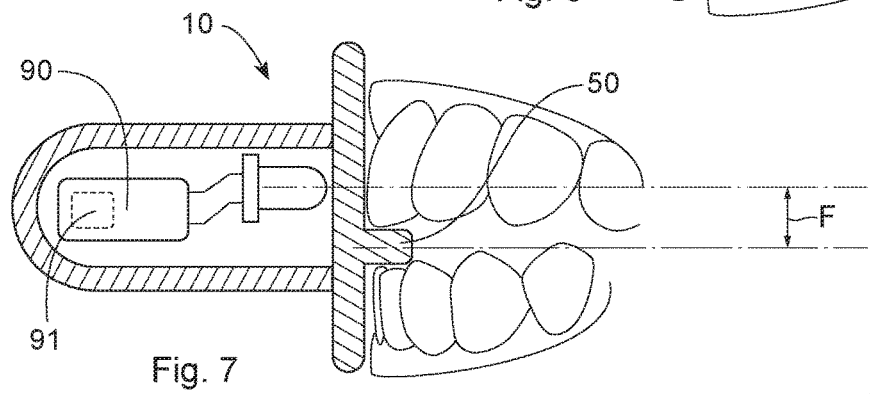
FIG. 7 schematically shows a cross-sectional side view of an embodiment of the device wherein the device is 180-degree invertible and is shown in a first orientation in which the light is primarily directed to maxillary teeth.
Figure 7A:
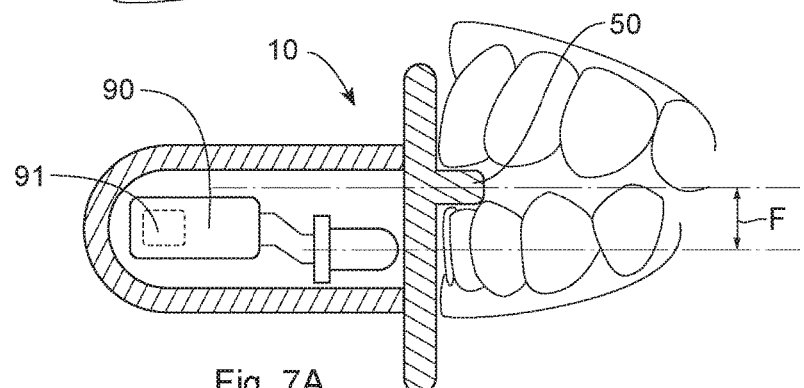
FIG. 7A schematically shows a cross-sectional side view of the invertible device shown in FIG. 7, wherein the device is in a second configuration in which the light is primarily directed to mandibular teeth.
Figure 8:
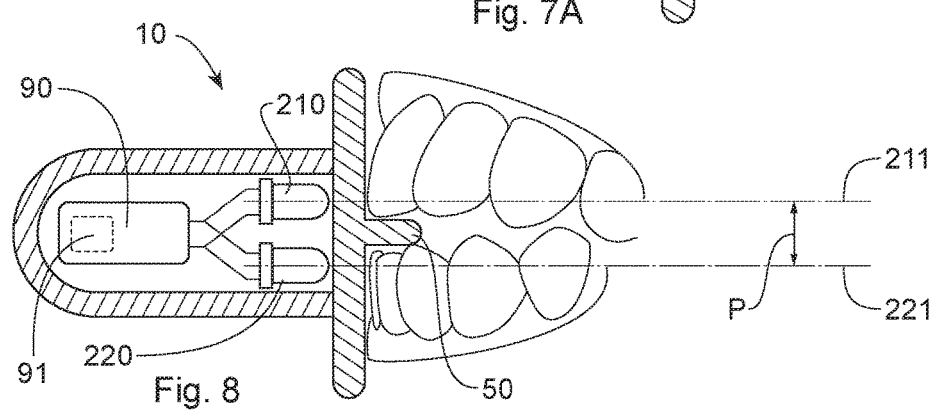
FIG. 8 schematically shows a cross-sectional side view of an embodiment of the device wherein the device comprises a first array of LEDs configured to deliver the light primarily to the maxillary teeth and a second array of LEDs configured to deliver the light primarily to the mandibular teeth.

The positioning feature 50 may be structured and configured to provide primarily a single-sided contact with maxillary teeth, which would indicate to the user that she should maintain a closed jaw with mandibular and maxillary teeth in an at-rest contact, as is shown in FIG. 6. Alternatively or additionally, the positioning feature 50 may be structured and configured to provide a dual or double-sided contact with maxillary and mandibular teeth, which would indicate to the user that she should bite the ledge during use of the device 10, as is shown in FIGS. 7-8. In some embodiments, the positioning feature 50 can be beneficially offset from the plane defined by the LED axes of foci by a distance F from about 1 mm to about 8 mm, and more specifically from about 3 mm to about 6 mm, as is shown in FIGS. 7 and 7A.

The arrangement of the LEDs 20 in the array can be beneficially provided to maximize an equal distribution of the light intensity among the teeth being treated. In one embodiment, an incremental angle A (FIG. 3) between primary foci 25 of two mutually adjacent inner LEDs 20a of the at least first array is between about 7 degrees and about 12 degrees. In another embodiment, the incremental angle between primary foci 25 of two mutually adjacent inner LEDs 20a of the at least first array is between about 9 degrees and about 10 degrees. An incremental angle B (FIG. 3) between the primary focus of at least one of the inner LEDs 20a of the at least first array and the primary focus 25 of at least one of the outer LEDs 20b adjacent thereto can be between about 7 degrees and about 12 degrees or between about 9 degrees and about 10 degrees. The incremental angles A and B do not have to be constant between the adjacent LEDs throughout the device. In some embodiments (not shown), the incremental angle A and/or B, can increase or decrease from the periphery to the center of the device or vice versa—to more precisely trace the shape of the user's jaw. One skilled in the art will appreciate that in embodiments where the incremental angle or angles between two adjacent LEDs change, additional focal points could be formed. For example, an embodiment (not shown) is contemplated in which each pair of mutually opposite LEDs (on both sides of the device 10 relative to the central axis X) has its own focal point.

In a further embodiment, the primary foci 25 of two mutually opposite end LEDs 20, which are the outer LEDs 20b, form therebetween an included angle C (FIG. 3) of from about 15 degrees to about 44 degrees. In another embodiment, the included angle C formed between the primary foci 25 of two mutually opposite end outer LEDs 20 can be from about 25 degrees to about 35 degrees.

The device 10 may include any suitable, either even or odd, number of LEDs 20, e.g., four, five, six, seven, eight, nine, ten or more LEDs altogether, wherein, e.g., from four to eight LEDs may comprise the inner LEDs 20a and from two to four LEDs may comprise the outer LEDs 20b. The exemplary device 10 illustrated herein includes six inner LEDs 20a and two outer LEDs 20b. One skilled in the art will appreciate that other suitable configurations of the device 10, comprising different numbers of the inner LEDs 20a and the outer LEDs 20b can be had—and are indeed fully contemplated.

FIG. 8 shows an exemplary embodiment of the device 10 comprising two arrays of LEDs: the first array of LEDs 210 and a second array of LEDs 220 adjacent to the first array of LEDs 210. The second array of LEDs 220 is disposed at a front side of the housing and in a second plane 221 different from the first plane 211, wherein the second array of LEDs is arranged to deliver blue visible light or near-visible UV light of at least a threshold intensity to substantially all anterior surfaces of anterior maxillary teeth or anterior mandibular teeth of the human jaw. The second array of LEDs 220 forms at least two intersecting arcs, each of which may be disposed in the second plane 221 and has its own focal point located outside the device 10, similarly to what has been described herein above with respect to the first array of LEDs.

Also analogously to the first array of LEDs described herein, the second array of LEDs 220 may comprise a plurality of outer LEDs 20b and a plurality of inner LEDs 20a, wherein the plurality of outer LEDs 20b of the second array 220 forms a second outer arc having a second outer focal point, and the plurality of inner LEDs 20a of the second array forms a second inner arc having a second inner focal point different from the second outer focal point, and wherein a distance between the second outer focal point and the device is greater than a distance between the second inner focal point and the device. (The second inner arc, the second outer arc, and the second focal points are not illustrated in detail herein—but will be readily visualized by a skilled artisan based on the illustrations of the similar elements, presented herein with respect to the first array of LEDs.) In various embodiments of the device 10 comprising two arrays of LEDs, examples of which are schematically shown in FIGS. 8-10, the first array of LEDs 210 can be configured to deliver the light primarily to the maxillary teeth and the second array of LEDs 220 can be configured to deliver the light primarily to the mandibular teeth, or vice versa.

In FIG. 8, the second plane 221, in which the second array of LEDs 220 is situated, is substantially parallel to the first plane 211, in which the first array of LEDs is situated. A distance P between the first plane 211 and the second plane 221 can be from about 0.5 cm to about 2.0 cm. In other embodiments, the first plane 211 and the second plane 221 can either converge or diverge. In an exemplary embodiment of FIG. 9, the planes 211 and 221 converge to form an angle V, which can be from about 0.5 degree to about 5 degree. In an exemplary embodiment of FIG. 10, the planes 211 and 221 diverge to form an angle W, which can be from about 0.5 degree to about 5 degree. The LEDs arrays' angled (non-parallel) arrangements of the types schematically shown in FIGS. 9 and 10 can be beneficial to direct light to those surfaces of the teeth being treated that are variably angled and or have atypically inclined surfaces.

Figure 14:
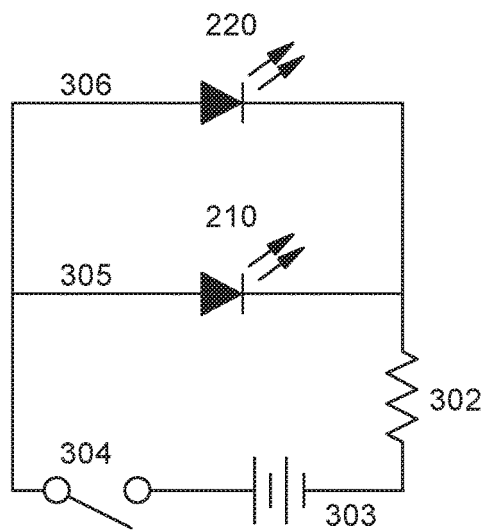
FIG. 14 is an exemplary electrical diagram that can be used in the device of the disclosure to simultaneously power the first array of LEDs and the second array of LEDs.

In embodiments comprising two arrays of LEDs, the first array of LEDs 210 and the second array of LEDs 220 can be structured to be powered either simultaneously or sequentially, depending on the process. An exemplary electrical diagram of the simultaneously powered arrays 210, 220 is schematically shown in FIG. 14, where a first circuits 305 and a second circuit 306 are connected in parallel, the first circuit 305 driving the first array of LEDs 210 and the second circuit 306 driving the second array of LEDs 220. Electric current, supplied by a battery 303 and limited by a resistor 302, travels through said circuits 305, 306. A switch 304 opens and closes both circuits simultaneously.

Figure 15:
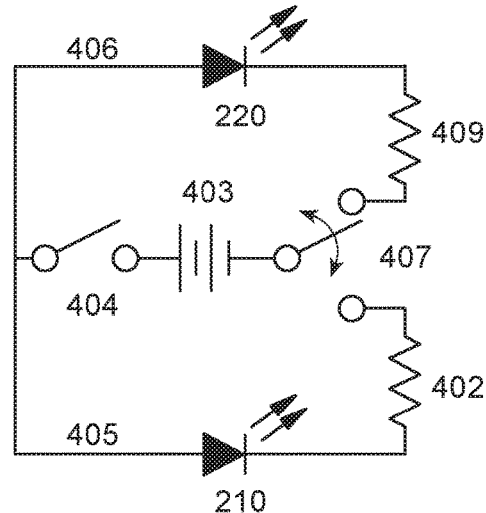
FIG. 15 is an exemplary electrical diagram that can be used in the device of the disclosure to sequentially power the first array of LEDs and the second array of LEDs.

An exemplary electrical diagram of the sequentially powered first and second arrays 210, 220 is schematically shown in FIG. 15, where a first circuit 405 and a second circuit 406 are connected in parallel and in isolation from one another by a toggle switch 407, configured to direct electric current from a battery 403 (upon closing of a switch 404) through either the first circuit 405 to drive the first array of LEDs 210 or the second circuit 406 to drive the second array of LEDs 220—but not permitting the current to flow simultaneously through both circuits 405, 406. In this embodiment, current-limiting resistors, e.g., a first resistor 402, and a second resistor 409, may be included separately and in series in each circuit, or between the battery and the toggle switch 407.

Figure 16:
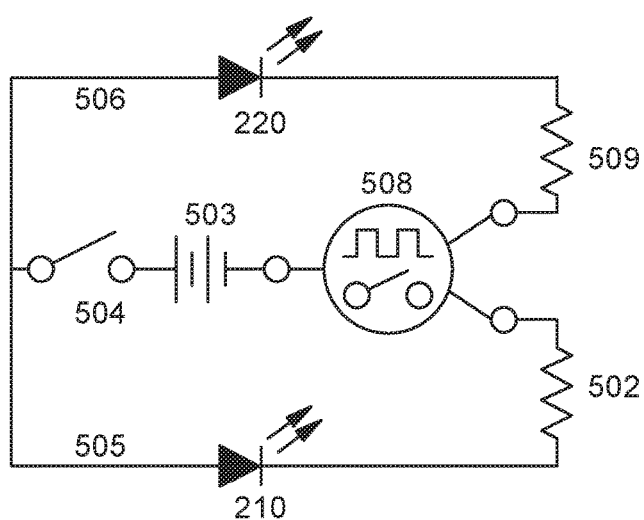
FIG. 16 is an exemplary electrical diagram that can be used in the device of the disclosure to power the first array of LEDs and the second array of LEDs in repetition at an established alternating frequency.

In a further exemplary embodiment, an electrical diagram of which is schematically shown in FIG. 16, the first and second arrays of LEDs 210, 220 can be powered in repetition at an established alternating frequency. A microcontroller or any other suitable mechanism 508 can be structured and configured to automatically and at a prescribed frequency direct electric current from a battery 503 (upon closing of a switch 504) alternately through first and second circuits 505, 506, to drive the first and second arrays of LEDs 210, 220, respectively. In this exemplary embodiment, each of the circuits 505, 506 may include a current-limiting resistor, e.g., 502 and 509 respectively.

Figure 12:
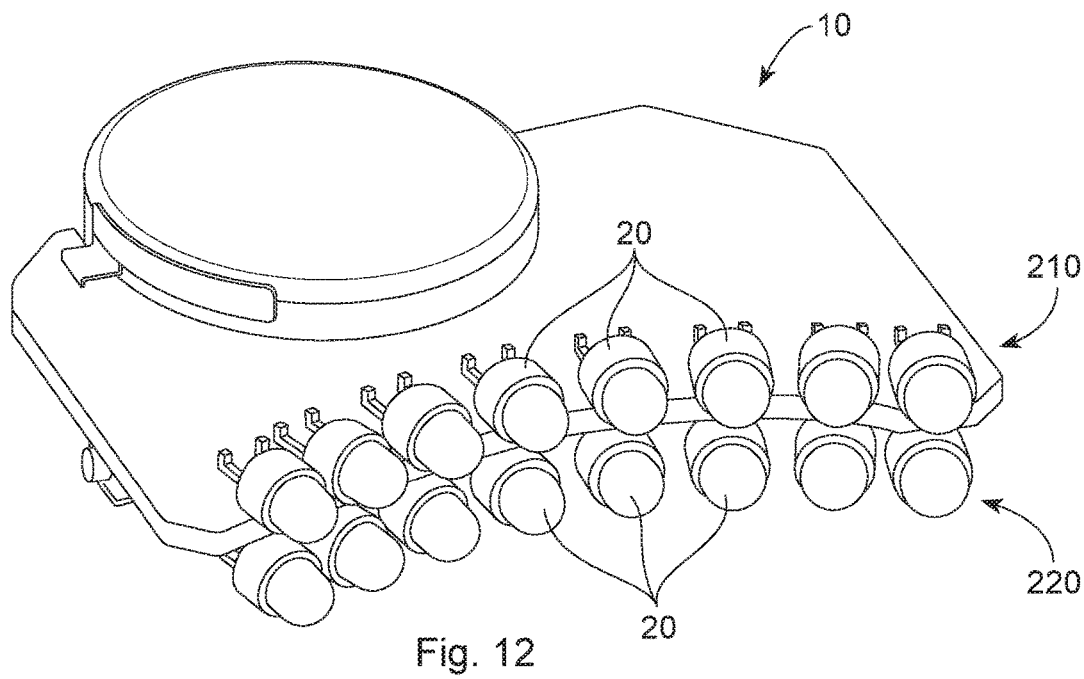
FIG. 12 schematically shows an axonometric view of an embodiment of the device comprising a first array of LEDs and a second array of LEDs wherein the individual LEDs of the first array are stacked relative to the individual LEDs of the second array.
Figure 13:
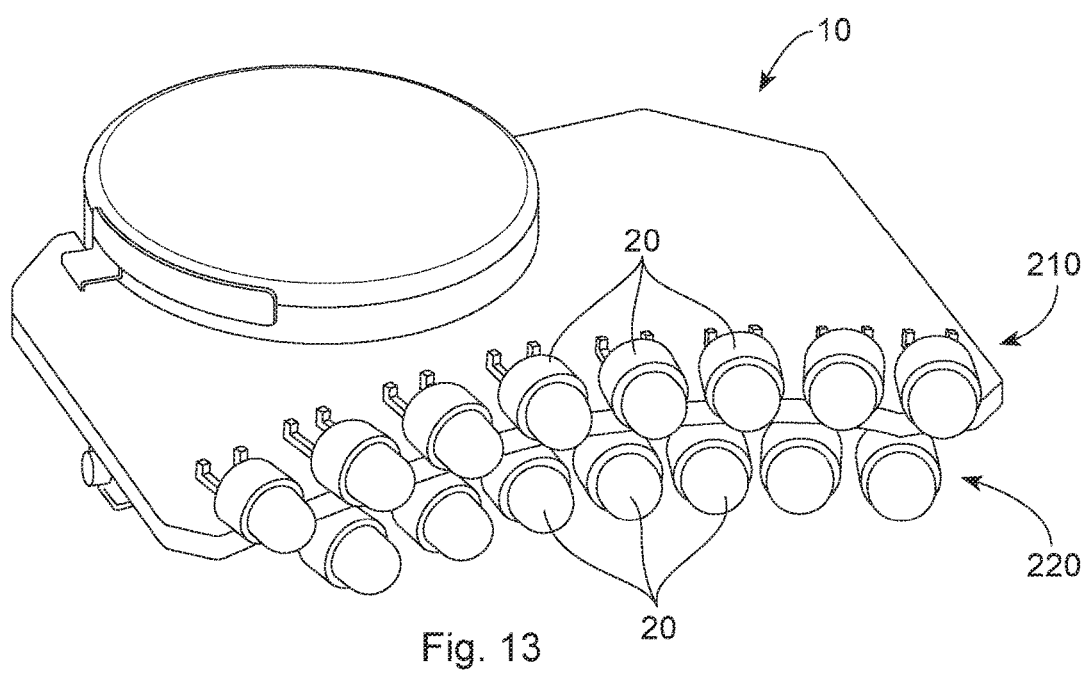
FIG. 13 schematically shows an axonometric view of an embodiment of the device comprising a first array of LEDs and a second array of LEDs wherein the individual LEDs of the first array are staggered relative to the individual LEDs of the second array.

An exemplary embodiment of the device 10 shown in FIG. 12 comprises two parallel arrays of LEDs, wherein the LEDs 20 of the second array 220 are unilaterally stacked relative to the LEDs 20 of the first array 210. In such an embodiment, the individual LEDs 20 of the first array 210 are aligned (vertically) with corresponding individual LEDs 20 of the second array 220. In another exemplary embodiment of the device 10, shown in FIG. 13, the LEDs 20 of the second array 220 are unilaterally staggered relative to the LEDs 20 of the first array 210. An embodiment (not shown) is contemplated in which some of the LEDs of the first and second arrays 210, 220 can be vertically aligned and some can be staggered.

A process for whitening includes several essential steps, including applying a whitening composition to the teeth and providing light-emitting diodes arranged in a certain configuration and powered to direct light to the teeth in a certain predetermined pattern. At least a first array of light-emitting diodes (LEDs) 20 disposed in a first plane and comprising a plurality of inner LEDs 20a and a plurality of outer LEDs 20b can be provided so that the plurality of inner LEDs 20a of the first array forms a first inner arc 30 having a first inner focal point 31, and the plurality of outer LEDs 20b forms a first outer arc 40 having a first outer focal point 41 different from the first inner focal point 31, FIG. 3. The first inner focal point 31 and the first outer focal point 41 are disposed on a first central axis X common to the plurality of inner LEDs 20a of the first array and the plurality of outer LEDs 20b of the first array.

A whitening composition can be applied to the anterior surfaces of at least six mandibular or maxillary anterior teeth. A number of tooth-whitening compositions may be utilized in the process of the disclosure described herein, such as, e.g., many peroxide-based tooth-whitening compositions with varying concentrations of peroxide may be provided. Other additives may also be provided in the composition, including, e.g., photosensitizing agents, gelling agents, humectants, pH-adjusting agents, stabilizing agents, desensitizing agents, and accelerating agents or bleach activators. The composition may be provided in the form of a viscous liquid, paste, gel, solution, or any other state or phase that may be applied to the teeth. Further, the tooth-whitening composition may be applied directly to the teeth, or may be contained by a tray placed over the teeth or provided on a strip of flexible material configured to be applied to the tooth surfaces to be whitened. Non-limiting examples of suitable tooth-whitening products include the strip-based tooth-whitening products described U.S. Pat. No. 6,949,240, and U.S. Application Publication No. 2003/0152528, the entire disclosures of which are incorporated herein by reference. The whitening composition can be maintained on the at least six teeth for a first (or delay) time period. During the first (or delay) period, a chemical whitening composition is maintained on the user's teeth without the application of light radiation.

After the first time period, light radiation is applied to the teeth in a subsequent second time period (or the light-radiation period). A light radiation comprising blue visible light or near-visible UV light of at least a threshold intensity from the least a first array of LEDs is directed to the anterior surfaces of the at least six teeth for a second time period. The first time period can beneficially have a duration that is at least 50% greater than a total duration of the first time period and the second time period combined. The light radiation may be applied through a translucent chemical whitening composition (and any corresponding translucent carrier for the composition, such as a tray or adhesive strip). In one embodiment of the process, the threshold light intensity at the teeth can beneficially be about 13 mW/cm$^2$. The first time period can be from 20 minutes to 120 minutes. The second time period can be from 2 minutes to 10 minutes.

The delay period can be greater than the light-radiation period, or greater than 50% of a total duration of the delay and light-radiation periods, such that the teeth are exposed to light radiation for less than half of the entire duration of the tooth-whitening treatment. The delay period may also be greater than about 60%, greater than about 70%, greater than about 80%, greater than about 90%, greater than about 95%, or greater than about 96%, or greater than about 97%, or greater than about 98%, or greater than about 99%, or greater than about 99.5%, or greater than about 99.9%, or between about 80% and about 90% of the total duration of the delay and light-radiation periods.

The resulting light intensity to which the teeth are exposed, i.e., the light intensity at the surface of the teeth, will depend, primarily, on the distance of the light source (LEDs 20) from the teeth and the energy output of the light source. The LEDs 20, can be disposed at a suitable distance from the teeth, e.g., from about 0.5 cm and about 3 cm. Exemplary ranges of light intensity at the teeth during the light-radiation period can be between about 0.05 mW/cm$^2$ and about 200 mW/cm$^2$, between about 0.1 mW/cm$^2$ and about 180 mW/cm$^2$, between about 1 mW/cm$^2$ and about 160 mW/cm$^2$, between about 5 mW/cm$^2$ and about 140 mW/cm$^2$, between about 10 mW/cm$^2$ and about 120 mW/cm$^2$, between about 20 mW/cm$^2$ and about 100 mW/cm$^2$, between about 30 mW/cm$^2$ and about 80 mW/cm$^2$, and between about 40 mW/cm$^2$ and about 60 mW/cm$^2$. In other examples, light intensity at the teeth during the light radiation period of a light enhanced tooth whitening process may be between about 40 mW/cm$^2$ and about 140 mW/cm$^2$, or approximately 42 mW/cm$^2$, or approximately mW/cm$^2$, or approximately 135 mW/cm$^2$. A particularly beneficial threshold light intensity at the teeth can be about 13 mW/cm$^2$.

The light emitted by the LEDs 20 may be selected to provide light radiation at a wavelength that is best absorbed by the tooth stains. Thus, the light radiation may be selected to be at a wavelength corresponding to a light color diametrically opposite the stain color, as identified for example on the 1976 CIE LAB color scale. Utilization of a diametrically opposite light color increases absorption of the light by the stain. Thus, yellow stains (as commonly present on teeth to be whitened) may better absorb blue light (approximately 380-520 nm). Thus, the light source may be selected to provide light radiation at a wavelength of about 400 nm to about 520 nm, or about 440 nm to about 490 nm, or an average wavelength of approximately 440 nm, or approximately 450 nm, or approximately 460 nm, or approximately 470 nm, or approximately 480 nm, or approximately 490 nm. Green stains, on the other hand, may better absorb red light, such as, e.g., light having a wavelength of about 600 nm to about 780 nm. Thus, a light source for use in whitening green stains may be selected to provide light radiation at a wavelength of about 600 nm to about 780 nm, or about 680 nm to about 720 nm, or an average wavelength of approximately 680 nm, or approximately 690 nm, or approximately 700 nm, or approximately 710 nm, or approximately 720 nm. In one embodiment, the light emitted by the LEDs during the process can have a frequency of from 350 nm to 470 nm.

Depending on the process, condition of the teeth, and other relevant factors, the first time period (or delay of the light radiation) and the second time period (or the period of light radiation) can be selected from a number of suitable ranges, as e.g., those disclosed in a commonly assigned US Patent Application Pub. No.: 2013/0295525 A1, the entire disclosure of which is incorporated herein by reference. The durations of the delay and light-radiation periods of the tooth whitening-treatment may be selected based on several factors; e.g., the delay period may be selected to allow the oxidizing or bleaching agent sufficient time to reach the tooth stains below the outer surfaces of the teeth before light activation of the stains.

For example, the delay period may range from about 2 minutes to about 480 minutes, or from about 5 minutes to about 55 minutes, or from about 15 minutes to about 25 minutes. In another embodiment, the delay period may be at least 1, 2, 5, 7, 10, 15, 20, 25, 30, 40, 50, or 60 minutes, but less than 480, 120, 90, 60, 50, 40, 30, 25, 20, 15, 10, 5, or 2 minutes. The light-radiation period may range for example from about 3 seconds to about 30 minutes, or from about 30 seconds to about 10 minutes, or from about 2 minutes to about 5 minutes. In another embodiment, the light radiation period may be at least 1, 2, 5, 7, 10, 15, 20, 25, 30, 40, 50, or 60 seconds, 2, 3, 4, minutes but less than 5, 4, 3, 2, or 1 minutes, 50, 40, 30, 25, 20, 15, 10, or 5 seconds.

The total duration of the delay and light-radiation periods may range, e.g., from about 4 minutes to about 500 minutes, or from about 10 minutes to about 60 minutes, or from about 15 minutes to about 30 minutes. In another embodiment, the total duration may be at least 4, 5, 7, 10, 15, 20, 25, 30, 40, 50, 60, 90, 120, 180, or 240 minutes, but less than 500, 480, 420, 360, 300, 240, 80, 120, 90, 60, 50, 40, 30, 20, or 15 minutes. Thus, in varying embodiments, the total duration may be at least 4, 5, 7, 10, 15, 20, 25, 30, 40, 50, 60, 90, 120, 180, or 240 minutes, but less than 500, 480, 420, 360, 300, 240, 80, 120, 90, 60, 50, 40, 30, 20, or 15 minutes; combined with a light-radiation period of at least 1, 2, 5, 7, 10, 15, 20, 25, 30, 40, 50, or 60 seconds, 2, 3, 4, minutes but less than 5, 4, 3, 2, or 1 minutes, 50, 40, 30, 25, 20, 15, 10, or 5 seconds; further combined with a delay period of at least 1, 2, 5, 7, 10, 15, 20, 25, 30, 40, 50, or 60 minutes, but less than 480, 120, 90, 60, 50, 40, 30, 25, 20, 15, 10, 5, or 2 minutes.

After the completion of the second time period, the whitening composition can be removed from the teeth. In some embodiments of the process, the tooth-whitening process may include an additional third time period, or second delay period, performed after the light-radiation period. During the third period, the tooth-whitening composition remains on the teeth without a light treatment, prior to removal. This second delay period may range, e.g., from about 1 minute to about 30 minutes. In one embodiment of the process, the whitening composition remaining on the tooth surfaces after the first time period can be removed from the tooth surfaces prior to the second time period.

In one embodiment, the process comprises at least a first treatment and a second treatment. The process may include a step of inverting the first array of LEDs by 180 degrees, from a first orientation to a second orientation, wherein in the first orientation (FIG. 7) the light is primarily directed to the maxillary teeth during the first treatment, and in the second orientation (FIG. 7A) the light is primarily directed to the mandibular teeth during the second treatment.

Figure 11:
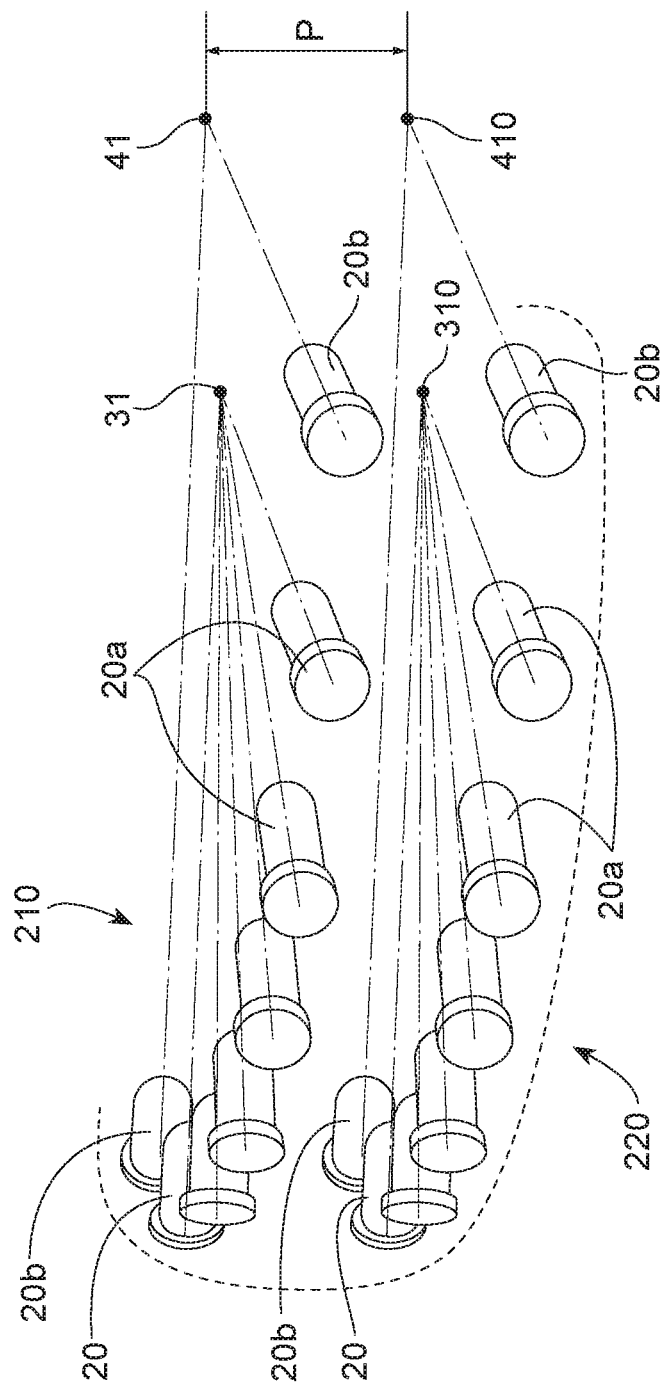
FIG. 11 schematically shows an axonometric view of an embodiment of an arrangement of the LEDs, the arrangement comprising a first array of LEDs and a second array of LEDs wherein the first array of LEDs is substantially parallel to the second array of LEDs.

In one embodiment of the process, a second array of LEDs 220 is provided, FIG. 11. The individual LEDs 20 in the first and second arrays can be either stacked, as is shown in FIG. 11, or, alternatively, staggered relative to one another, as is described herein above with reference to FIGS. 9 and 10. A mixed stacked/staggered pattern (not shown), where some of the LEDs can be stacked while others staggered, is also contemplated. The second array of LEDs 220 is adjacent to the first array of LEDs 210, wherein the second array of LEDs 220 is disposed in a second plane different from the first plane formed by the first array of LEDs 210, FIG. 11. Like the first array of LEDs 210, the second array of LEDs 220 comprises a plurality of inner LEDs 20*a* and a plurality of outer LEDs 20*b*. The plurality of inner LEDs 20*a* of the second array 220 forms a second inner arc having a second inner focal point 310, and the plurality of outer LEDs 20*b* of the second array 220 can form a second outer arc having a second outer focal point 410 different from the second inner focal point 310. The second inner focal point 310 and the second outer focal point 410 can be disposed on a second central axis common to the plurality of inner LEDs 20*a* of the second array 220 and the plurality of outer LEDs 20*b* of the second array 220.

In an embodiment of the process utilizing two arrays of LEDs 210, 220, the process may comprise directing, after the first time period, a light radiation comprising blue visible light or near-visible UV light of at least a threshold intensity from the second array of LEDs 220 for the second time period to the anterior surfaces of the at least six teeth, the first time period having a duration greater than 50% of a total duration of the first time period and the second time period. In such an embodiment, the first array of LEDs 210 delivers the light primarily to the maxillary teeth and the second array of LEDs 220 delivers the light primarily to the mandibular teeth.

The light from the first array 210 and the second array 220 can be delivered in various patterns and sequences. In one embodiment of the process, e.g., the first array of LEDs 210 and the second array of LEDs 220 illuminate the teeth simultaneously. In another exemplary embodiment, the first array of LEDs 210 and the second array of LEDs 220 illuminate the teeth sequentially. In still another exemplary embodiment of the process, the first array of LEDs 210 and the second array of LEDs 220 illuminate the teeth in repetition at an established alternating frequency.

While particular embodiments have been illustrated and described herein, various other changes and modifications may be made without departing from the spirit and scope of the invention. Moreover, although various aspects of the invention have been described herein, such aspects need not be utilized in combination. It is therefore intended to cover in the appended claims all such changes and modifications that are within the scope of the invention.

The terms "substantially," "essentially," "about," "approximately," and the like, as may be used herein, represent the inherent degree of uncertainty that may be attributed to any quantitative comparison, value, measurement, or other representation. These terms also represent the degree by which a quantitative representation may vary from a stated reference without resulting in a change in the basic function of the subject matter at issue. Further, the dimensions and values disclosed herein are not to be understood as being strictly limited to the exact numerical values recited. Instead, unless otherwise specified, each such dimension is intended to mean both the recited value and a functionally equivalent range surrounding that value. For example, values disclosed as "3 cm" or "50 degrees" are intended to mean, respectively, "about 3 cm" or "about 50 degrees."

The disclosure of every document cited herein, including any cross-referenced or related patent or application, and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein—or that it alone, or in any combination with any other reference or references, teaches, suggests, or discloses any such invention. Further, to the extent that any meaning or definition of a term in this document conflicts with any meaning or definition of the same or similar term in a document incorporated by reference, the meaning or definition assigned to or contextually implied by that term in this document shall govern.

What is claimed is:

1. A portable self-contained tooth-whitening device comprising:
   a compact housing structured and configured to be held in a fixed position adjacent to a human jaw during use;
   at least a first array of light-emitting diodes (LEDs) disposed in a first plane at a front side of the housing and arranged to deliver blue visible light or near-visible UV light of at least a threshold intensity to anterior surfaces of anterior maxillary teeth or anterior mandibular teeth of the human jaw, each of the LEDs having an axis of a primary focus, wherein the at least first array of LEDs comprises a plurality of outer LEDs and a plurality of inner LEDs, wherein the plurality of outer LEDs is arranged in a first outer arc having a first outer focal point formed by the axes of primary foci of the plurality of the outer LEDs, and the plurality of inner LEDs is arranged in a first inner arc different from the first outer arc and having a first inner focal point formed by the axes of primary foci of the plurality of the inner LEDs, wherein there is a distance between the first outer focal point and the first inner focal point, and wherein the first outer arc, the first inner arc, the first outer focal point, and the first inner focal point are disposed in the first plane;
   at least one battery cell powering the array of LEDs.

2. The device of claim 1, wherein a distance between the first outer focal point and the device is greater than a distance between the first inner focal point and the device.

3. The device of claim 2, wherein the distance between the first outer focal point and the device is at least twice the distance between the first inner focal point and the device.

4. The device of claim 1, wherein an incremental angle between the axes of primary foci of two mutually adjacent inner LEDs of the first array is between about 7 degrees and about 12 degrees.

5. The device of claim 1, wherein an incremental angle between an axis of a primary focus of at least one of the inner LEDs of the first array and an axis of a primary focus of at least one of the outer LEDs of the first array adjacent thereto is between about 7 degrees and about 12 degrees.

6. The device of claim 1, wherein the axes of primary foci of two mutually opposite end LEDs of the first array form therebetween an included angle of from about 15 degrees to about 44 degrees, wherein the two mutually opposite end LEDs of the first array are the outer LEDs of the first array.

7. The device of claim 1, wherein the plurality of inner LEDs of the first array includes from 4 to 6 LEDs.

8. The device of claim 1, wherein the plurality of outer LEDs of the first array includes from 2 to 4 LEDs.

9. The device of claim 1, wherein the device comprises a positioning feature structured and configured to cause the first array of LEDs to direct the light primarily to either maxillary teeth or mandibular teeth.

10. The device of claim 9, wherein the positioning feature comprises a protrusion structured and configured to fit between the maxillary teeth or and the mandibular teeth.

11. The device of claim 10, wherein the device is invertible 180 degrees, from a first orientation to a second orientation, wherein in the first orientation the light is primarily directed to the maxillary teeth while in the second orientation the light is primarily directed to the mandibular teeth.

12. The device of claim 1, wherein the device comprises a second array of LEDs adjacent to the first array of LEDs, wherein the second array of LEDs is disposed at a front side of the housing and in a second plane different from the first plane, wherein the second array of LEDs is arranged to deliver blue visible light or near-visible UV light of at least a threshold intensity to anterior surfaces of anterior maxillary teeth or anterior mandibular teeth of the human jaw, wherein the second array of LEDs forms at least two intersecting arcs, each of which is disposed in the second plane and has its own focal point located outside the device.

13. The device of claim 12, wherein the second array of LEDs comprises a plurality of outer LEDs and a plurality of inner LEDS, wherein the plurality of outer LEDs of the second array forms a second outer arc having a second outer focal point, and the plurality of inner LEDs of the second array forms a second inner arc having a second inner focal point different from the second outer focal point, and wherein a distance between the second outer focal point and the device is greater than a distance between the second inner focal point and the device.

14. The device of claim 12, wherein the second plane is parallel to the first plane.

15. The device of claim 12, wherein a distance between the first plane and the second plane is from about 0.5 cm to about 2.0 cm.

16. The device of claim 12, wherein the first array of LEDs is configured to deliver the light primarily to the maxillary teeth and the second array of LEDs is configured to deliver the light primarily to the mandibular teeth.

17. The device of claim 12, wherein powering of the first array of LEDs and the second array of LEDs is selected from the group consisting of simultaneous powering, sequential powering, and powering at an established alternating frequency.

18. The device of claim 1, wherein a total weight of the device is not greater than 100 g.

19. The device of claim 12, wherein the second array of LEDs is parallel to the first array of LEDs and wherein the LEDs of the second array are either unilaterally stacked or unilaterally staggered relative to the LEDs of the first array.

20. The device of claim 14, wherein the second plane and the first plane are not parallel to one another.

* * * * *